United States Patent [19]

Bone et al.

[11] Patent Number: 4,810,352
[45] Date of Patent: Mar. 7, 1989

[54] ELECTROCHEMICAL SENSORS

[75] Inventors: David J. Bone, Braintree; Trevor K. Gibbs, Rayne; Howard A. Buckenham, Brentwood; Paul Gotley, North Weald, all of United Kingdom

[73] Assignee: Neotronics Limited, Takely, United Kingdom

[21] Appl. No.: 44,142

[22] Filed: Apr. 30, 1987

[30] Foreign Application Priority Data

May 9, 1986 [GB] United Kingdom ............... 8611397

[51] Int. Cl.⁴ ............................................. G01N 27/46
[52] U.S. Cl. ................................. 204/432; 204/415
[58] Field of Search ............... 204/1 P, 415, 431, 432

[56] References Cited

U.S. PATENT DOCUMENTS

| 3,000,804 | 9/1961 | Cahoon et al. | 204/435 |
| 3,208,927 | 9/1965 | Arthur et al. | 204/435 |
| 4,132,616 | 1/1979 | Tantram et al. | 204/415 |
| 4,324,632 | 4/1982 | Tantram et al. | 204/415 |
| 4,446,000 | 5/1984 | Cullinane, Jr. . | |
| 4,633,704 | 1/1987 | Tantram et al. . | |

FOREIGN PATENT DOCUMENTS 1200595 7/1970 United Kingdom .

Primary Examiner—T. Tung
Attorney, Agent, or Firm—Dennis P. Clarke

[57] ABSTRACT

An electrochemical gas sensor for detecting the amount of a gas or vapor in an atmosphere is described having a sensing electrode and a barrier limiting the rate of access of the gas or vapor to the sensing electrode, the barrier being made of ceramics material and having an inwardly-tapering shape.

17 Claims, 2 Drawing Sheets

ELECTROCHEMICAL SENSORS

The present invention relates to sensors for electrochemically active gases or vapours and especially for gaseous oxygen.

In known gas sensors operating on the limiting current principle, the gas to be sensed is reacted at a working electrode which, in the case of an oxygen sensor, is a cathode. Access of gas to the working (or sensing) electrode is limited by a barrier placed between the atmosphere and the electrode and the amount of the gas crossing the barrier and therefore being reduced at the cathode is proportional to the amount of the gas in the atmosphere and the output current from the sensor is proportional to the amount of the gas present in the atmosphere. Several forms of barrier are known and they generally fall into two categories.

(a) semi-permeable membranes in which the electroactive gas dissolves in the material of the membrane and crosses the membrane in the solution phase, see for example GB Nos. 1 200 595 and 1 385 201.

(b) gas phase diffusion barriers in which the gas has to diffuse through pores or narrow orifices to reach the cathode. Porous membranes, which may be made of PTFE, fall into this category. Also, the gas phase diffusion barrier can be in the form of a hole or a capillary, see for example GB No. 1 450 776, GB No. 1 316 751, GB No. 1 318 189 and U.S. Pat. No. 3,394,069.

The rate of diffusion across semi-permeable membranes is very sensitive to temperature and the tension of the membrane and often gas phase diffusion barriers are preferred. However, these suffer from some very serious problems:

(1) When the sensor is taken from a cold to a warm environment, water vapour condenses which can close off the pores in the gas-phase diffusion barrier and so the sensor ceases to function.

(2) The rate of transport of gas across a gas phase diffusion barrier is dependent on the ambient temperature and therefore the sensor output varies with temperature. This can be dealt with by incorporating a thermistor in the sensor circuit to adjust the output current according to the ambient temperature, but it would be more satisfactory to provide a sensor whose output varied only sightly (if at all) with temperature.

(3) When subjected to positive pressure shocks, e.g. the pressure wave inside a car caused by the car door being slammed shut, the pressure wave causes a momentary peak in the sensor output. Also, when subject to negative pressure shocks, e.g. when a sensor is taken through an air lock, the sensor output can suddenly drop. Sensors are frequently installed in devices that monitor the sensor output and give a warning alarm if the output suddenly rises or falls and the pressure shocks can trigger the alarm unnecessarily.

(4) When the sensor is hit or otherwise moved suddenly and violently, there can be a surge of gas through the barrier causing an output peak similar to that described in (3) above and causing the same problems.

(5) Many gas sensors cannot work at high atmospheric pressures e.g. above 2 bar.

The present invention provides a gas sensor which is not liable to the above problems or at least in which the above problems are less acute than in known gas sensors.

According to the present invention, there is provided a gas or vapour sensor comprising a sensing electrode and a barrier limiting the rate of access of gas from the ambient atmosphere to the electrode, wherein the barrier is a body of sinter material having an outer surface facing the atmosphere and an inner surface facing the sensing electrode, the body being so shaped that the area of its flow cross-section is largest at the said outer surface. The "flow cross section" is the cross section (including the inner surface) taken perpendicular to the overall direction of gas flow through the body.

It is especially preferred that the inner surface of the sinter body should be smaller in area than the outer surface and/or any other flow cross-section of the body and the body may thus taper, preferably linearly, from the outer to the inner surface. Our preferred shape is frusto conical (tapering in the direction towards the sensing electrode). However, many other shapes can be used, e.g. frusto pyramidal or funnel-shaped. The use of shoulders or necks in the body can give rise to areas through which gas does not diffuse smoothly and so it is preferred to avoid shapes having shoulders or necks but such shapes can be used if they, for example, simplify the manufacture of the sinter body or its installation into the sensor housing.

The outer and inner surfaces of the sinter body are preferably flat but can be concave or convex if it is desired to increase their surface area.

The ratio of the area of the outer surface to the area of the smallest flow cross-section is preferably at least 2:1, more preferably at least 3:1, and advantageously at least 6:1. There is no upper limit to the ratio, although for ease of manufacture it is preferably not greater than 25:1. We have found an area of 9:1 works well.

The body is preferably made of ceramics sinter but a metal sinter can also be used. The preferred material for the sinter is alumina, magnesia, stabilized zirconia or silicon nitride, although theoretically any ceramics material may be used.

The porosity of the sinter depends on the intended application of the sensor and should be chosen so that, for the application involved, the amount of gas reaching the sensing electrode gives an electrical output that is large enough to be measured by the circuits of the associated monitor but not so large that the life of the sensor is unduly short; the preferred current range is approximately 0.1 to 5 mA, typically 0.5 to 1.5 mA and preferably 0.5 to 1 mA. Thus, if one were measuring the oxygen content of an atmosphere consisting almost totally of oxygen, a sinter body of lower porosity would be required than that required when measuring the oxygen content of air. We contemplate that the porosity of the sinter should be between 2% and 35%, e.g. 4% to 25%. In air, we believe that the porosity should be 6 to 25%, e.g. 8% to 21% and most preferably about 14% (to provide a relatively low output) or about 20% (to provide a relatively high current). By 'porosity' we mean the percentage by volume of the sinter body that is occupied by pores.

The length of the sinter body between the inner and outer faces affects the response time and is preferably less than 10 mm, e.g. less than 6 mm and the preferred range is 2 to 4 mm.

The pore size in the sinter should be large enough to avoid forming a Klinkenber-type body and the preferred range is 0.1 to 10 $\mu$m, e.g. 0.5 to 5 $\mu$m and advantageously about 1 $\mu$m.

The sensor of the present invention is preferably of the well known galvanic type, and the anode material should be chosen to provide a potential difference between it and the sensing electrode such that the sensor works ont he limiting current principle i.e. the potential is sufficiently large to reduce all the gas to be detected that reaches the cathode but not so large as to reduce other active species and in particular not sufficiently large to reduce (or oxidise) the electrolyte. Such anode materials include lead, which is the preferred material, cadmium or bismuth. Alternatively, the sensor can be polarographic in which case the potential applied between the sensing electrode and the reference/counter electrodes should be maintained at a level that ensures operation on the current limiting principle. For a discussion of the current limiting principle, reference may be made to British Pat. Nos. 1,571,282 and 1,200,595.

The cathode is preferably a layer of catalyst applied to the back surface of a hydrophobic porous sheet. i.e. the surface facing the electrolyte. The catalyst material may be platinum and/or iridium and/or silver and/or palladium and/or rutherium and/or gold. The hydrophobic sheet is preferably a fluoropolymer e.g. polytetrafluoroethylene (PTFE). As well as carrying the catalyst layer, the hydrophobic sheet also prevents escape of water from the electrolyte and hence prevents the sensor from drying out. It may be that the single catalyst-carrying hydrophobic sheet is not sufficient for waterproofing the sensor and reducing water loss to an acceptable level, in which case one or more further porous hydrophobic sheets may be provided between the cathode support sheet and the porous sintered body.

Since the hydrophobic sheets are porous, they can provide a barrier to the migration of the gas being detected to the catalyst material. The porosity of the sinter body and of the hydrophobic sheet(s) must be matched in a sensor according to the present invention so that the rate of migration of gas to the catalyst cathode material is primarily determined by the porous sinter body and not by the hydrophobic sheet(s). This can easily be determined by adding a further sheet made of identical material to the catalyst support sheet (or the further hydrophobic sheet(s), if different) between the cathode and the sinter body and observing whether there is any change in the response time of the sensor (the response time is the time delay between a change in the composition of the atmosphere being sensed and the consequent change in the sensor output). The diffusion of gas in the sensor can be said to be determined by the sinter body if the response time on the addition of the additional porous sheet changes by less than about 10%. When the sensor contains two or more hydrophobic sheets of different compositions, the above test should be conducted in respect of each sheet separately.

The shape of the sinter body is very important for the avoidance of blockage by condensation. Sensors of the present invention having frustoconical sinter bodies have been tested over a wide range of temperature and humidity changes that are generally encountered and we have not discovered any combination of temperature and humidity change that causes a blockage in the sensor; in contrast, known oxygen sensors under identical changes of temperature and humidity cease to function because they become blocked by condensation. When instead of a frustoconical sinter body, a cylindrical sinter body is used made of identical material and having a diameter equal to that of the outer surface of the frustoconical sinter body, the cylindrical sinter body is readily blocked by condensation. Likewise, a frustoconical sinter body also becomes blocked if the small surface faces the atmosphere.

When the sinter body is made of ceramic material, we have discovered that the sensor has a low temperature coefficient, i.e. its output does not vary appreciably with changes in ambient temperature. Metallic sinter bodies have a larger temperature coefficient but it is still low compared to known sensors.

The sensor of the present invention does not give appreciable output fluctuations when subject to physical shock or to pressure waves. Also, sensors of the present invention can work at raised atmospheric pressure, e.g. 2 to 4 bar.

The sensor of the present invention is primarily intended for safety applications in which breathing air is monitored and a warming given if the oxygen level falls to a dangerous level but it can be used in other applications too.

The present invention will now be described, by way of example only, with reference to the accompanying drawing in which:

FIG. 2 is an axial cross-section showing part of the sensor of

Figure 1:
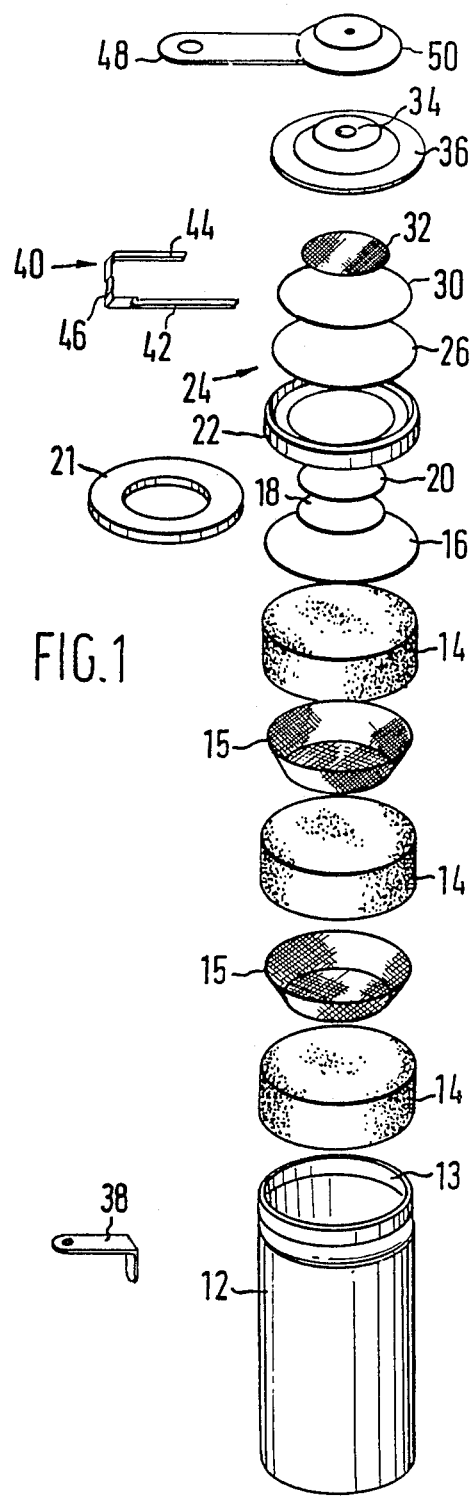
FIG. 1 is an exploded perspective view of a sensor of the present invention.

FIG. 1 in a partly assembled form, and

Figure 2:
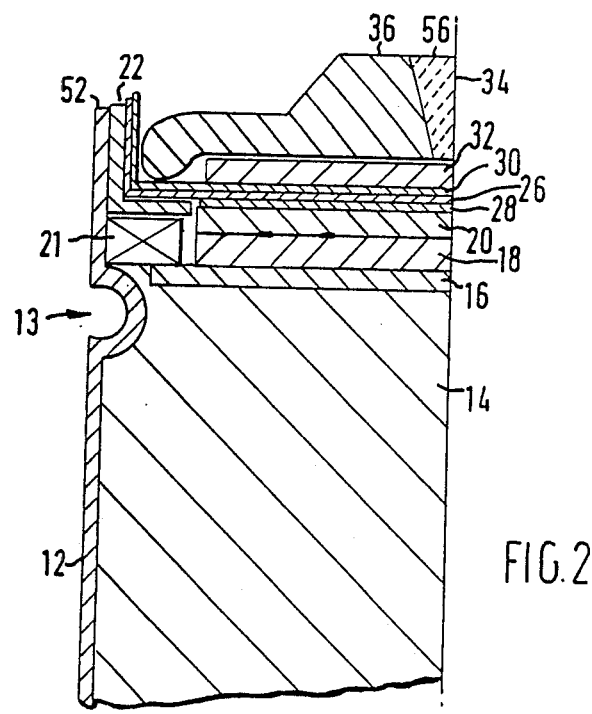
Figure 3:
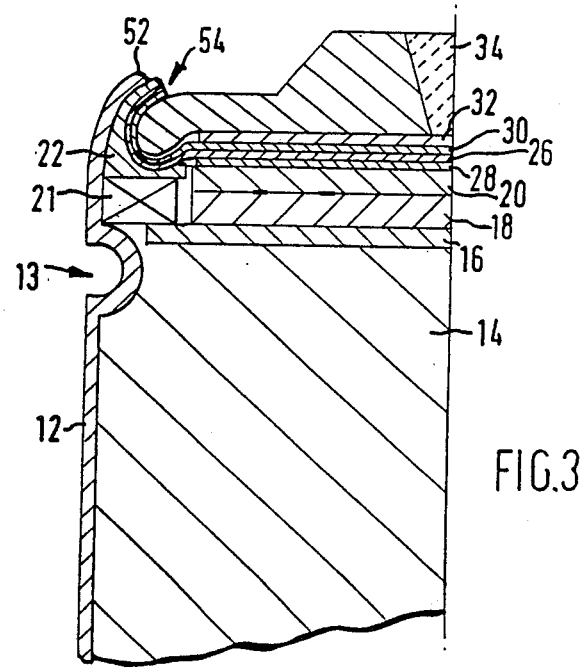

FIG. 3 is the same as FIG. 2 but the sensor is in an assembled form.

Referring to FIG. 1, an oxygen sensor is shown which is housed in a nickel-plated mild steel can 12 of the type frequently used in nickel cadmium storage batteries. The can 12 is crimped around its circumference near its open end to provide an internal rib 13 (see FIG. 2). The cap is filled, in order from the bottom to the top of the can, with three cylinders of lead wood 14, the second and third of which are seated in nickel mesh baskets 15 to ensure good electrical contact with the can. Above the third lead cylinder 14, there are one large- and two small- diameter separators 16, 18 and 20 made of polyamide or fibreglass material. The separators are steeped in electrolyte for the cell which we prefer to be an alkaline electrolyte e.g. concentrated KOH. The two small separators 18 and 20 are located inside a nickel-plated washer 12 and the large separator 16 contacts the bottom surface of the washer 21. The washer itself sits on the rib 13 of the can. Next, there is a nylon insulating ring 22, which has an L-shape cross section; it may be of the type often used in nickel-cadmium cell batteries. Ring 22 provides electrical insulation between, on the one hand, the lead cylinders 14 and the can 12 and, on the other hand, a cathode 24. The cathode 24 is a disc 26 of polytetrafluoroethylene (PTFE) on the bottom of which there is a layer composed of a mixture of sintered PTFE powder and a catalyst for the reduction of oxygen, e.g. platinum and/or silver; the catalyst layer is shown by the reference number 28 in FIG. 2. The PTFE disc preferably has a pore size of 0.1 to 2 $\mu$m e.g. 2 $\mu$m and we use a type that is commercially available from W. L. Gore and Associates (U.K.) Limited under the trade name 'Electrode tape' and has a pore size of 1 $\mu$m. Optionally, a further disc of Electrode tape 30 is located above cathode disc 26 and functions, together with disc 26, to prevent evaporation of electrolyte from the sensor. Above PTFE disc 30, there is a mat 32, which is optional, but when present it disperses the gas or vapour entering the sensor through a porous plug 34 in the top cap 36 of the sensor. The top cap is made of nickel or nickel-plated mild steel and, as stated, has a centrally-located porous plug 34 made of sinter material and preferably of ceramics sinter. The plug 34 is in the shape of an inverted frusto cone and is fixed in the top plate 36 by any suitable material that produces an air-tight seal between the plug 34 and the top plate 36 and that does not penetrate into the porous plug. Adhesive, e.g. epoxy resin, impact adhesive, potting compound, or solder may be used for this purpose.

The electrical connections to the sensor are as follows: an anode terminal 38 is welded onto the can 12 which in turn is in contact with the lead anode material 14. The cathode connection is provided by a metal strip 40 having one arm 42 which lies against, and in electrical contact with, the cathode catalyst layer 28 and a second arm 44 that contacts the underside of top cap 36; a connecting portion 46 is located inside insulating ring 22 to prevent any contact with the can 12. A cathode terminal 48 is provided on a dust cover 50 which is in electrical contact with top cap 36. The dust cover 50 has a central hole filled with highly porous material that allows air to pass to the porous sinter plug 34 but filters out dust and similar materials.

The arrangement of the individual components in the sensor is more easily seen in FIG. 2 which uses identical reference numbers to those used in FIG. 1. The metal strip 40, the dust cover 50 and the anode terminal 38 have been omitted for clarity. The sensor in FIG. 2 in in a semi-finished state and is finished by rolling the top edge 52 of the can over the top cap 36 to provide a gas-tight seal 54 (see FIG. 3). The seal is obtained because the edge 52 of the can presses the top cap 36 down and compresses the inulating ring 22 and the PTFE discs 26 and 30 between it and the washer 21. Because the ring 22 and the discs 26 and 28 are resilient, the seal that can be obtained in practice is good.

FIG. 2 clearly shows the frusto conical shape of the porous sinter plug 34. It is made of alumina or magnesia of 12% porosity, its outer surface 56 is 3 mm in diameter, its inner surface 56 is 1 mm in diameter and it is 3 mm long. The porous ceramics sinter body can be made by standard ceramics technology. Likewise, metal sinters are known for other applications and can be made by standard techniques.

In operation, air diffuses through the porous sinter plug 34, is dispersed by porous mat 32, diffuses across PTFE discs 26 and 30 and the oxygen component is reduced immediately it reaches the catalyst layer 28. The reduction takes place at the interface between the catalyst and the alkaline KOH electrolyte to form hydroxyl ions; simultaneously, an oxidation reaction takes place at the lead anode. As a consequence of these reactions, a current flows between the anode and cathode terminals 38 and 40 that is proportional to the amount of oxygen reduced at the cathode which in turn is proportional to the amount of oxygen in the atmosphere.

We claim:

1. An electrochemical sensor for determining the amount of an electrochemically active gas or vapour in an atmosphere, which sensor comprises a sensing electrode and a barrier limiting the rate of access of gas or vapour from the atmosphere to the sensing electrode, the barrier being a body of porous sinter material having an outer surface facing the atmosphere and an inner surface facing the sensing electrode, the cross-section are of the body taken perpendicularly to the overall direction of gas flow decreases from said outer surface to said inner surface said sensing electrode comprising a layer of catalyst material applied on the side of a sheet of hydrophobic material that is remote from the sinter body.
2. A sensor as claimed in claim 1, wherein the smallest cross-section is the inner surface.
3. A sensor as claimed in claim 1, wherein the ratio of the area of the outer surface to the area of the smallest cross-section is at least 2:1.
4. A sensor as claimed in claim 3, wherein the ratio of the area of the outer surface to the area of the smallest cross-section is at least 3:1.
5. A sensor as claimed in claim 3, wherein the ratio of the area of the outer surface to the area of the smallest cross-section is at least 6:1.
6. A sensor as claimed in claim 1, wherein the sinter body is made from a material selected from the group consisting of ceramics sinter and metal sinter.
7. A sensor as claimed in claim 1, wherein the porosity of the sinter is in the range of from 2% to 35%.
8. A sensor as claimed in claim 7, wherein the porosity of the sinter is in the range of from 4% to 25%.
9. A sensor as claimed in claim 8, wherein the porosity of the sinter is in the range of from 6% to 20%.
10. A sensor as claimed in claim 1, wherein the length of the body between the inner surface and the outer surface thereof is less than 10 mm.
11. A sensor as claimed in claim 10, wherein the length of the body between the inner surface and the outer surface thereof is less than 6 mm.
12. A sensor as claimed in claim 10, wherein the length of the body between the inner surface and the outer surface thereof is between 2 and 4 mm.
13. A sensor as claimed in claim 1, wherein the pores in the sinter body have a pore size in the range of from 0.1 to 10 $\mu$m.
14. A sensor as claimed in claim 13, wherein the said pore size is in the range of from 0.5 to 5 $\mu$m.
15. A sensor as claimed in claim 1, wherein the said hydrophobic material is polytetrafluoroethylene.
16. A sensor as claimed in claim 1, wherein the sinter body has a funnel shape.
17. A sensor as claimed in claim 16, wherein the sinter body has an inverted frustoconical shape.

* * * * *

UNITED STATES PATENT AND TRADEMARK OFFICE
CERTIFICATE OF CORRECTION

PATENT NO. : 4,810,352

DATED : March 7, 1989

INVENTOR(S) : David J. Bone; Trevor K. Gibbs; Howard A. Buckenham; Paul Gotley

It is certified that error appears in the above-identified patent and that said Letters Patent is hereby corrected as shown below:

Claim 1, column 6, line 9, "are" should be --area--.

Claim 1, column 6, line 11, before "said", second occurrence, insert -- and --.

Signed and Sealed this

Twenty-ninth Day of August, 1989

Attest:

DONALD J. QUIGG

*Attesting Officer*   *Commissioner of Patents and Trademarks*